US010874089B2

(12) United States Patent
Hurley et al.

(10) Patent No.: US 10,874,089 B2
(45) Date of Patent: Dec. 29, 2020

(54) TEMPERATURE MONITORING DEVICE AND A SYSTEM FOR MONITORING ANIMAL TEMPERATURE

(71) Applicant: Epona Biotec Ltd., Kowloon (HK)

(72) Inventors: Michael John Hurley, Kowloon (HK); Adrian Cecil Poon, Kowloon (HK)

(73) Assignee: Epona Biotec Limited, Kowloon (HK)

( * ) Notice: Subject to any disclaimer, the term of this patent is extended or adjusted under 35 U.S.C. 154(b) by 0 days.

(21) Appl. No.: 16/309,713

(22) PCT Filed: Nov. 30, 2017

(86) PCT No.: PCT/CN2017/113731
§ 371 (c)(1),
(2) Date: Dec. 13, 2018

(87) PCT Pub. No.: WO2018/099414
PCT Pub. Date: Jun. 7, 2018

(65) Prior Publication Data
US 2019/0133088 A1 May 9, 2019

(30) Foreign Application Priority Data
Nov. 30, 2016 (HK) .................................. 16113643

(51) Int. Cl.
*A01K 29/00* (2006.01)
*A61B 5/01* (2006.01)
*G08C 21/00* (2006.01)
*H04Q 9/00* (2006.01)
*A61B 5/00* (2006.01)
(Continued)

(52) U.S. Cl.
CPC .......... *A01K 29/005* (2013.01); *A61B 5/0008* (2013.01); *A61B 5/0022* (2013.01); *A61B 5/01* (2013.01); *A61B 5/02055* (2013.01); *A61B 5/02438* (2013.01); *A61B 5/11* (2013.01); *A61B 5/1118* (2013.01); *G08C 21/00* (2013.01); *H04Q 9/00* (2013.01); *A61B 2503/40* (2013.01); *H04Q 2209/43* (2013.01); *H04Q 2209/86* (2013.01)

(58) Field of Classification Search
CPC ................... A61B 2560/0242; A61B 10/0012
USPC ..................................................... 340/573.3
See application file for complete search history.

(56) References Cited

U.S. PATENT DOCUMENTS 4,643,193 A 2/1987 DeMarzo
6,113,539 A 9/2000 Ridenour
(Continued)

FOREIGN PATENT DOCUMENTS

CN 203563516 4/2014
CN 203736168 7/2014
(Continued)

*Primary Examiner* — Fabricio R Murillo Garcia
(74) *Attorney, Agent, or Firm* — Renner, Kenner, Greive, Bobak, Taylor & Weber (57) ABSTRACT

A temperature monitoring device for an animal such as a horse including a housing including a body, and a base with an aperture; a temperature sensor at least partly extending through the aperture; wireless communication for transmitting temperature measurements to a mobile device; wherein the base is provided with first attachment for attaching the base to the animal such that the temperature sensor contacts the animal; and the body is provided with second attachment to secure the body to the base via the first attachment.

17 Claims, 6 Drawing Sheets

(51) Int. Cl.
*A61B 5/0205* (2006.01)
*A61B 5/024* (2006.01)
*A61B 5/11* (2006.01)

(56) References Cited

U.S. PATENT DOCUMENTS

| | | | |
|---|---|---|---|
| 2013/0060098 A1* | 3/2013 | Thomsen | A61B 5/02028 600/301 |
| 2017/0196503 A1* | 7/2017 | Narayan | A61B 5/0402 |
| 2017/0325426 A1 | 11/2017 | Brosh et al. | |
| 2018/0014512 A1* | 1/2018 | Arabani | H04N 7/185 |
| 2019/0274551 A1* | 9/2019 | Barton-Sweeney | G16H 40/63 |

FOREIGN PATENT DOCUMENTS

| | | |
|---|---|---|
| CN | 104146689 | 11/2014 |
| CN | 106069859 | 11/2016 |
| WO | 2006094513 | 9/2006 |
| WO | 2014188273 | 11/2014 |

\* cited by examiner

TEMPERATURE MONITORING DEVICE AND A SYSTEM FOR MONITORING ANIMAL TEMPERATURE

FIELD OF INVENTION

The invention relates to a device and method for monitoring the temperature of animals, and particularly, although not exclusively for the monitoring of the temperatures of animals during transportation.

BACKGROUND

Animals such as cows, sheep, horses and cattle, as well as companion animals such as dogs and cats, are often transported vast distances as necessitated by their owners. Animals such as cattle may be transported by ships from a country of export to a country of import for farming or food purposes. Animals such as dogs or other types of companion animals may be transported as part of a relocation process of its owner. Horses are also regularly transported from various international destinations to participate in events, competitions and for racing.

Despite efforts that are made by owners to ensure the animals are comfortable during their transportation by road, rail, sea, or air, animals are nonetheless subject to significant amounts of stress when they are travelling. In turn, the stress suffered by the animals further lowers their resistances to diseases which are already common in transportation environments.

This transportation stress causes significant economic loss on the part of owners or commercial or industrial activities that are operate around these animals. The suffering of the animal requires medical intervention, which may increase the cost to transport the animals. In certain industries such as agriculture, the health of the animals has a significant impact on production of food items due to public health laws or customs quarantine requirements.

SUMMARY OF INVENTION

In an aspect of the invention, there is provided a temperature monitoring device comprising:
  a housing including a body, and a base with an aperture;
  temperature measurement means including a temperature sensor at least partly extending through the aperture;
  wireless communication means for transmitting temperature measurements;
  wherein the base is provided with first attachment means for attaching the base to an animal such that the temperature sensor contacts the animal; and
  the body is provided with second attachment means to secure the body to the base via the first attachment means.

Advantageously the temperature of the animal, such as a horse can be continuously monitored during transit to determine if there are any signs of illness, so that in such circumstances treatment can be given at the earliest opportunity.

In one embodiment the first attachment means is in the form of a layer with an outer portion extending beyond the underside of the base. Typically the body includes a peripheral margin, and the second attachment means is provided in the form of a ring which fits over the body of the housing and includes an outer portion which extends beyond the margin, the outer portion of the ring being securable to the outer portion of the layer. Thus the body and base are sandwiched between and secured together by the respective attachment means.

In one embodiment, the base and the first attachment means are integrally formed as a single planar base layer.

In one embodiment the attachment means comprises acrylic adhesive such as a pressure sensitive adhesive. Typically the attachment means is medical tape or dry surgical tape. Dry surgical tape such as 3M Multipore® has a dual layer structure which keeps the surface layer dry, with a porous outer layer and water repellent inner layer, the inner layer including a hypoallergenic acrylic adhesive for securing to the skin of an animal. In one embodiment, the single planar base layer is made from medical tape or dry surgical tape.

In one embodiment the temperature measurement means and wireless communication means are located substantially within the body of the housing, and are able to measure and transmit cutaneous skin temperature readings continuously. Typically the wireless communication means includes an antenna which extends beyond the housing.

In one embodiment the wireless communication means includes a transmitter capable of any or any combination of WiFi®, Bluetooth®, Infra-red, and/or the like.

In one embodiment the body includes a battery and a pull tab connected to a plastic spacer strip between the battery and the electrical contacts, such that removing the plastic spacer strip via the pull tab activates the device.

In one embodiment the housing is shaped and sized to fit on the ventral aspect of the tail immediately caudal to the animal's anus.

This position is particularly advantageous in that at this location the large coccygeal artery is located superficially beneath the skin, therefore providing cutaneous skin temperature readings that are more closely correlated with the core body temperature of the animal, than at other cutaneous locations. There is also little hair that may grow at this location and thus adherence of the device to the skin is also optimal.

In one embodiment the animal is a horse, but it will be appreciated that the device may be adapted to suit other animals.

In one embodiment the receiver comprises an application on a mobile device. Typically the device is a mobile phone running the Android® operating system, but it will be appreciated that other operating systems may be used.

In one embodiment the application includes any or any combination of the following indicators: normal temperature range, top end of normal temperature range, fever, critically high fever, low temperature, no signal, and/or the like.

In one embodiment the mobile device transmits an alert for selected indicators to a predetermined person.

In one embodiment the device further includes means for measuring the heart rate of the animal and/or an accelerometer. Typically the data from these means are transmitted and monitored in a similar way to the temperature measurements.

In accordance with a second aspect of the present invention, there is provided a system for monitoring animal temperature comprising:
  one or more temperature monitoring devices arranged to record the animal temperatures over a predefined time period;
  a communication gateway arranged to communicate with the one or more temperature monitoring devices to receive the animal temperatures over the predefined time period; and a reporting engine arranged to process the animal temperatures for reporting a condition of the animal.

In an embodiment of the second aspect, the one or more temperature monitoring devices include a temperature sensor arranged to be placed on or adjacent to a part of the animal to measure the temperature of the animal.

In an embodiment of the second aspect, the one or more temperature monitoring devices further includes a motion sensor arranged to detect a physical movement of the animal.

In an embodiment of the second aspect, the one or more temperature monitoring devices further includes a heart rate sensor arranged to measure the heart rate of the animal.

In an embodiment of the second aspect, the temperature sensor, motion sensor and the heart rate sensor are controlled by a micro-controller.

In one embodiment, the one or more temperature monitoring device includes a biosensor which is arranged to detect and quantify levels of specific biomarkers in the blood or interstitial fluid, preferably in real-time. These specific bio-markers may be relevant to identifying illness, and monitoring response of the animal to treatment. In a horse, for example, important biomarkers of inflammation include the Acute Phase Proteins (Such as Serum Amyloid A [SAA] and Fibrinogen).

In one example embodiment, the biosensor is arranged to detect viruses, bacteria, antibodies, cancerous cells, and other biochemical markers in the blood or interstitial fluid, that may be indicative of an infection, response to infection, or disease or damage to organ systems. This point-of-care, real-time, health monitoring system will revolutionize the way that disease in horses and other species are identified, treated and monitored.

Preferably, this biosensor may be implemented with a microchip sensor which has a plurality of micro-needles, arranged to be inserted or otherwise in contact with the animal, such as a horse, to measure the level of biomarker in the blood or interstitial fluid of the animal. Once these micro-needles are able to be contacted with the blood or interstitial fluid of the animal, the biomarkers can be detected by the microchip sensor. In an embodiment of the second aspect, the micro-controller is disposed within the temperature monitoring device.

In an embodiment of the second aspect, the heart rate sensor is arranged to communicate with the micro-controller via a filter device arranged to filter the results of the heart rate sensor.

In an embodiment of the second aspect, the temperature of the animal, the physical movement of the animal and the heart rate of the animal is processed by the reporting engine to determine the condition of the animal.

In an embodiment of the second aspect, the reporting engine is arranged to present the condition of the animal in a graphic format.

In an embodiment of the second aspect, the reporting engine is arranged to generate an alert on the bases of the condition of the animal.

In an embodiment of the second aspect, the temperature monitoring device includes a housing and a base arranged to engage the housing to the animal.

In an embodiment of the second aspect, the base includes an annular flange arranged to adhere the housing to the animal.

In an embodiment of the second aspect, the base includes the annular flange includes a layer of medical grade tape arranged to adhere to the animal.

In an embodiment of the second aspect, the housing houses the temperature sensor, the motion sensor and the heart rate sensor.

In an embodiment of the second aspect, the housing includes a protective layer arranged to cushion the temperature sensor, the motion sensor and the heart rate sensor from physical force.

In one embodiment, the housing includes an insulating layer arranged to insulate the cutaneous temperature sensor from the external environmental. This is advantageous in that the insulation may improve the correlation of the measured cutaneous temperature to that of the true core body temperature.

In further aspect of the invention, there is provided a temperature monitoring device comprising:

a housing including a body with a peripheral margin, and a base with an aperture;

a ring of dry surgical tape secured to the margin with an outer portion extending laterally beyond the margin;

a layer of dry surgical tape provided on the underside of the base with an outer portion extending laterally beyond the base;

the layer of dry surgical tape having an aperture aligned with the aperture in the base;

a temperature sensor at least partly extending from the body through the apertures in the base and tape;

a wireless transmitter and an antenna at least partly extending from the housing for transmitting temperature measurements from the temperature sensor to a wireless device comprising a monitoring application;

wherein the outer portion of the ring of dry surgical tape is adhered to the outer portion of the layer of dry surgical tape to secure the body to the base; and the layer of dry surgical tape can adhere to a horse at a location beneath the horse's tail such that the temperature sensor contacts the skin of the horse.

BRIEF DESCRIPTION OF DRAWINGS

It will be convenient to further describe the present invention with respect to the accompanying drawings that illustrate possible arrangements of the invention. Other arrangements of the invention are possible, and consequently the particularity of the accompanying drawings is not to be understood as superseding the generality of the preceding description of the invention.

DETAILED DESCRIPTION

With reference to FIGS. 1-3, 4A and 4B, there is illustrated a temperature monitoring device (2) comprising: a housing (4) including a body (8), and a base (10) with an aperture (12);

temperature measurement means including a temperature sensor (20) at least partly extending through the aperture (12); wireless communication means (22) for transmitting temperature measurements; wherein the base (10) is provided with first attachment means (14) for attaching the base (10) to an animal such that the temperature sensor (20) contacts the animal; and the body (8) is provided with second attachment means (18) to secure the body (8) to the base (10) via the first attachment means (14).

In this embodiment, the temperature monitoring device 2 comprises a housing 4 with a peripheral margin 6, and a rounded body 8. The device also includes a substantially flat base 10 with an aperture 12. In one example embodiment, the device 2 is arranged to monitor the temperature of an animal, such as a horse, cow, bull, goat, deer, dog, cat or any other cattle or animal, over a time period and process, store or transmit this temperature information to determine, assist in determining or presenting the information for further assessment or diagnoses of the animal. Preferably, the temperature monitoring device 2 is further arranged to transmit this temperature information to a computer or computing device, including a computer server, computer, laptop computer, tablet computer, smart phone, wearable device, communication device, cloud based device or any other devices having a computational processor, accessible storage/memory and input/output device or gateway to receive the temperature from the temperature monitoring device 2 for processing, presentation (graphic, text or otherwise), storage or transmission.

Example embodiments of the temperature monitoring device 2, may be used by applying the device onto an animal to monitor the temperature of the animal over a period of time. When the device 2 is applied onto the animal, the temperature sensor 20 is arranged to measure the temperature of the animal. This measurement can be taken in a discrete manner over time with a frequency that is deemed necessary, or it can be taken continuously over time. The temperature measurements are then processed, either on a computer processor integrated within the device 2, or preferably, on a centralised computing device which is in communications with the device 2.

These temperature measurements may then be used to determine the condition of the animal, including the health and status of the animal. In many situations, where an animal becomes infected with a bacterial or viral infection or is suffering from stress or other medical condition, the animal may experience a fever as a symptom of this condition. In turn, by analysing the temperature measurements, the health and status of the animal can be analysed and a diagnosis can be made so that appropriate treatment may be performed.

Example embodiments of the temperature monitor device 2 may be advantageous in that animals can be monitored frequently or continuously when they would otherwise not be monitored and thus allowing their owners, operators or caretakers to prescribe an appropriate treatment quickly. In examples where the device 2 is used in the horse racing industry, it is common for race horses to be transported vast distances in preparation for a race or event. Whilst attempts may be made by their caretakers to ensure the horse is put into a most comfortable arrangement for transportation so as to optimize the temperature, humidity, space, noise, vibration and the like to minimize the stress on the horse, certain aspects of the transportation may nevertheless cause the horse discomfort. In these example situations, should a race horse fall sick during the transportation process, its caretaker may prescribe the appropriate treatment to the horse, such as relocation, termination of the transportation, provision of rest, provision of food or prescription of medications or stimulants to the horse as soon as a condition is detected, thus allowing the caretaker to take appropriate and fast actions to treat the horse without any undue delay.

In this example embodiment, the device 2 is implemented to include a base which is arranged to have an attachment means in the form of a layer of dry surgical tape 14 provided on and extending beyond the underside of the base. This dry surgical tape 14 may, in some example, be made from a porous material having adhesives on one side of the tape so as to allow the tape to adhere to the surface of the animal. The dry surgical tape 14 is preferably porous so as to minimize any discomfort on the animal and may be made from an anti-allergic or organic material so as to minimize the risk of irritation on the animal. When the device is ready to be applied to an animal, a liner paper 16 layer which covers the adhesive side of the tape 14 can be removed from the tape to expose the adhesive, which allows the device to be stuck to the skin of an animal. In examples where the application is on a horse, the caretaker can simply remove the liner paper 16 and place the device 2 on the horse, with the dry surgical tape 14 base bonding itself to the skin of the horse.

A ring of dry surgical tape 18, which as shown in this example embodiment, appears as an annular flange with around the housing, is also provided, secured to and extending laterally beyond the margin of the housing, such that the extended portion of the ring fits over the body and adheres to the layer of surgical tape extending from the base, thereby securing the base to the housing by sandwiching the same between the surgical tapes.

Figure 3:
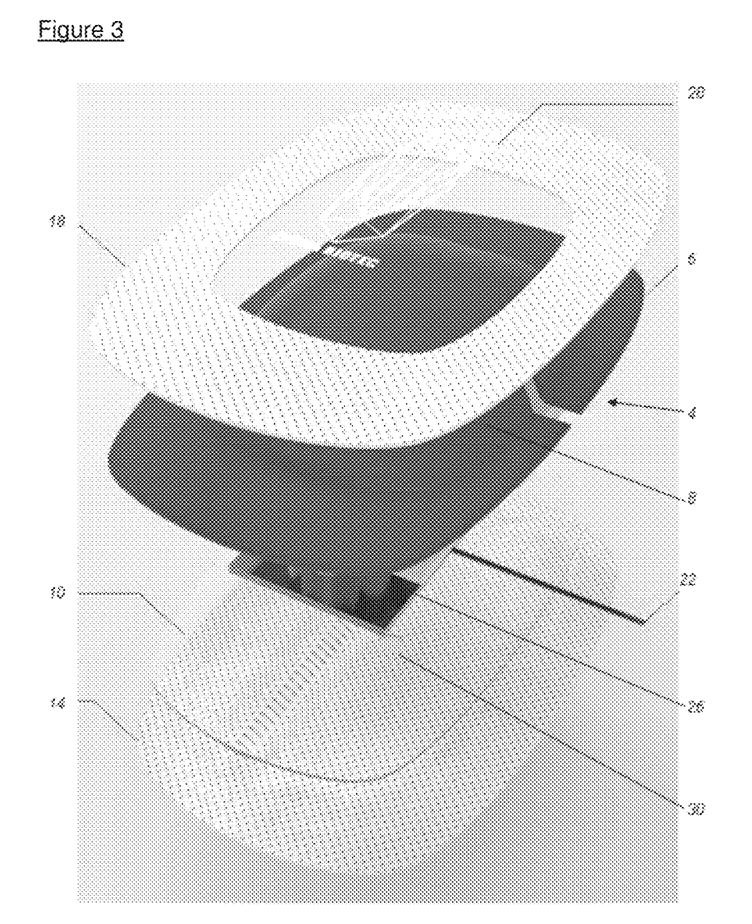
FIG. 3 is an exploded view of a temperature monitoring device.

As shown in the exploded diagram of FIG. 3, the device 2 includes a Printed Circuit Board (PCB) 26 within the body 8, on which is mounted a temperature sensor 20, which extends from the body 8 through aligned apertures 12, 30 in the base and surgical tape layer, and an antenna 22 which extends laterally from the housing 4 for wireless communication of data such as temperature readings. The PCB is arranged to provide the processing functionalities to the device 2, and will include a logical circuit, programmable array, microprocessor or micro controller to control the operation of the device 2 as well as control the operation of the temperature sensor 42 and other functional sensors and components, such as accelerometer 44, and heart rate monitors 46 which can assist in monitoring the movement and heart rate of the animal. In turn, these sensors provide further data for monitoring and diagnosing of the animal.

Furthermore, the PCB may also have on board memory/computer storage 40 and a communication gateway, including an antenna 22 arranged to store computing instructions, recorded data and to provide the communication functionality to the device 2. The PCB may also be arranged to form an electrical connection to a battery 36 or power source, which will power the PCB and its components for a suitable duration. The battery 36 may be rechargeable or as shown in an example embodiment suitable for use with race horses, the battery 36 may be a single use battery cell, which can supply power for a set duration (e.g. 4 days) typical of a transportation of a race horse from one country to another.

Advantageously, examples of the embodiments of the temperature monitoring device may be suitable implemented to be single use or disposable. Advantageously, the device may be used for short-term monitoring in very specific situations such as, but not limited to:
  the detection of Shipping Fever or other causes of pyrexia
    in a horses undergoing transportation;

monitoring horses in the pen-operative period (early detection of a surgical infection); monitoring horses during infectious disease outbreaks (such as Equine Influenza, Strangles, Herpes);

for monitoring body temperature during drug and vaccine trials;

for the prediction of foaling or ovulation in the mare; monitoring the response to treatment of sick horses under veterinary care;

monitoring healthy horses immediately before competition to detect abnormal temperature fluctuations that may indicate a developing illness or infection that may affect performance;

for use in quarantine facilities to monitor horses for infectious disease.

An advantage of the device being made to be for a single use, or disposable is that the device will not become a vector for diseases, since it may come into contact with biohazardous pathogens of each animal when it is in use.

Returning to FIG. 3, as shown in this example embodiment of the device 2, the PCB may also be constructed to be surrounded by a layer of foam or other resilient material such as rubber or sealant which is arranged to substantially surround or enclose the PCB within the body. This is advantageous in that the PCB is protected or cushioned from impact or shock or moisture when in use, as animals may move about during transportation, any such exposure to water, impact or shock from their movement would be dampened or absorbed from being applied directly to the components of the PCB, and thus minimize the probability of the PCB from being damaged.

In example embodiments, where the device 2 is used with a race horse, the preferred location for the device 2 when applied to the horse is just underneath the tail of the race horse, above the anus, where the skin is hairless. This position provides the optimum attachment and temperature readings for most horses, although other positions are also possible. In other animals, alternative positions may also be used to measure the temperature of the animal.

In this example embodiment, the body includes a pull tab 24 connected to a plastic or other insulator spacer strip (not shown) between a battery (not shown) and the corresponding electrical contacts (not shown), such that removing the plastic spacer strip via the pull tab activates the device as the battery would then form an electrical contact with the electrical components of the device 2, such as the PCB with the sensors and components thereon. This is advantageous in that the battery can be placed within the device 2 during manufacturing and shipping, thus allowing the end user to simply remove the tab 24 when activating the device, whilst ensuring that the battery is not discharged when the device is yet to be used or is in storage.

A vinyl sticker 28 in the shape of a brand or logo may also be provided on the housing so as to identify the brand or identity of the device 2. In other embodiments, the vinyl sticker 28 may also be replaced with an identifier which can be in the form of a sticker or directly printed onto the housing, such as a barcode or QR code sticker which can be used to identify the device attached to the animal. This is particularly useful in examples whereby a user can scan the device with a scanner or camera to obtain access to the animal information, including identity and other related information.

Figure 1:
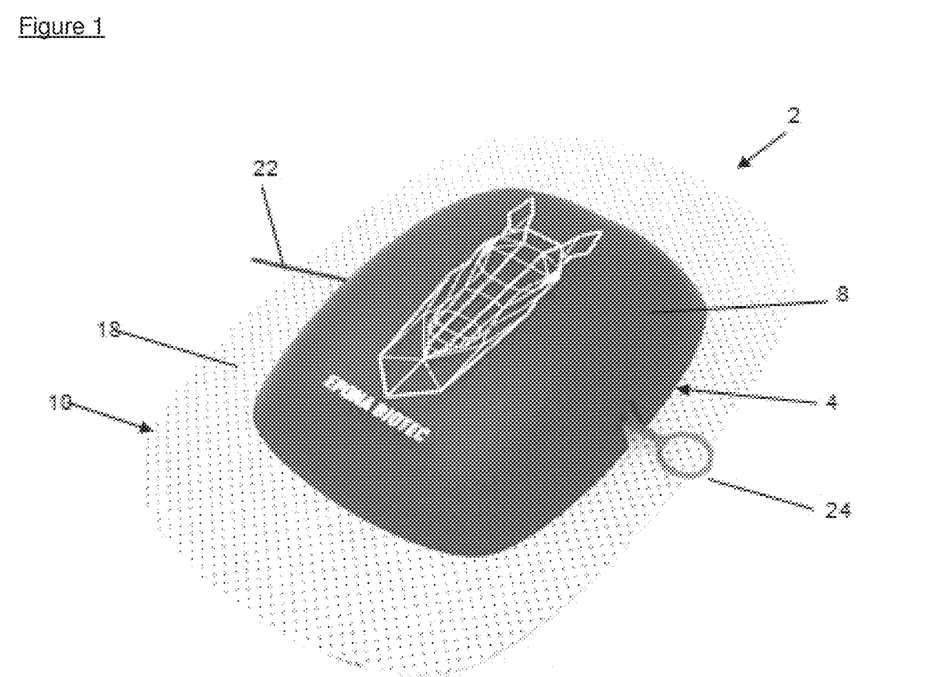
FIG. 1 is a perspective view from above of a temperature monitoring device according to an embodiment of the invention.
Figure 2:
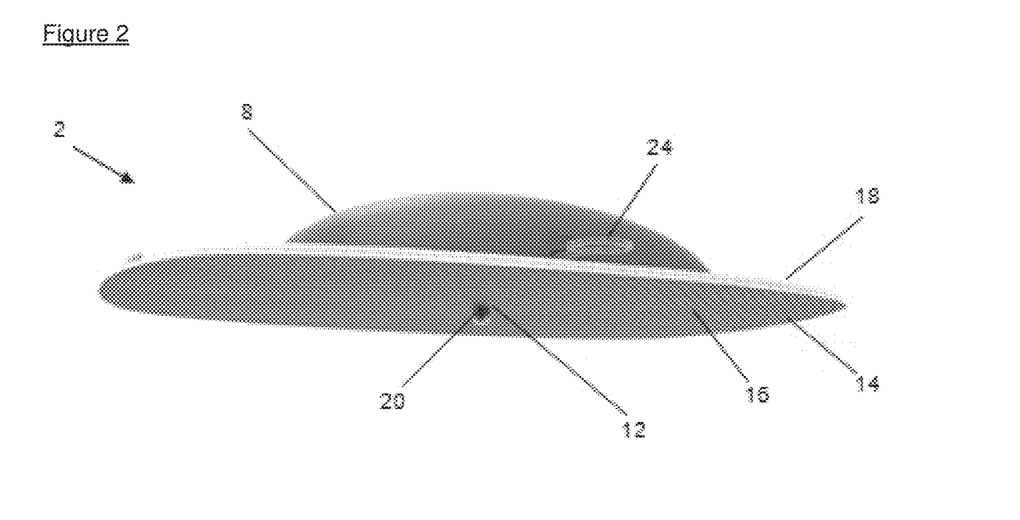
FIG. 2 is a perspective view from the side of a temperature monitoring device.
Figure 4A:
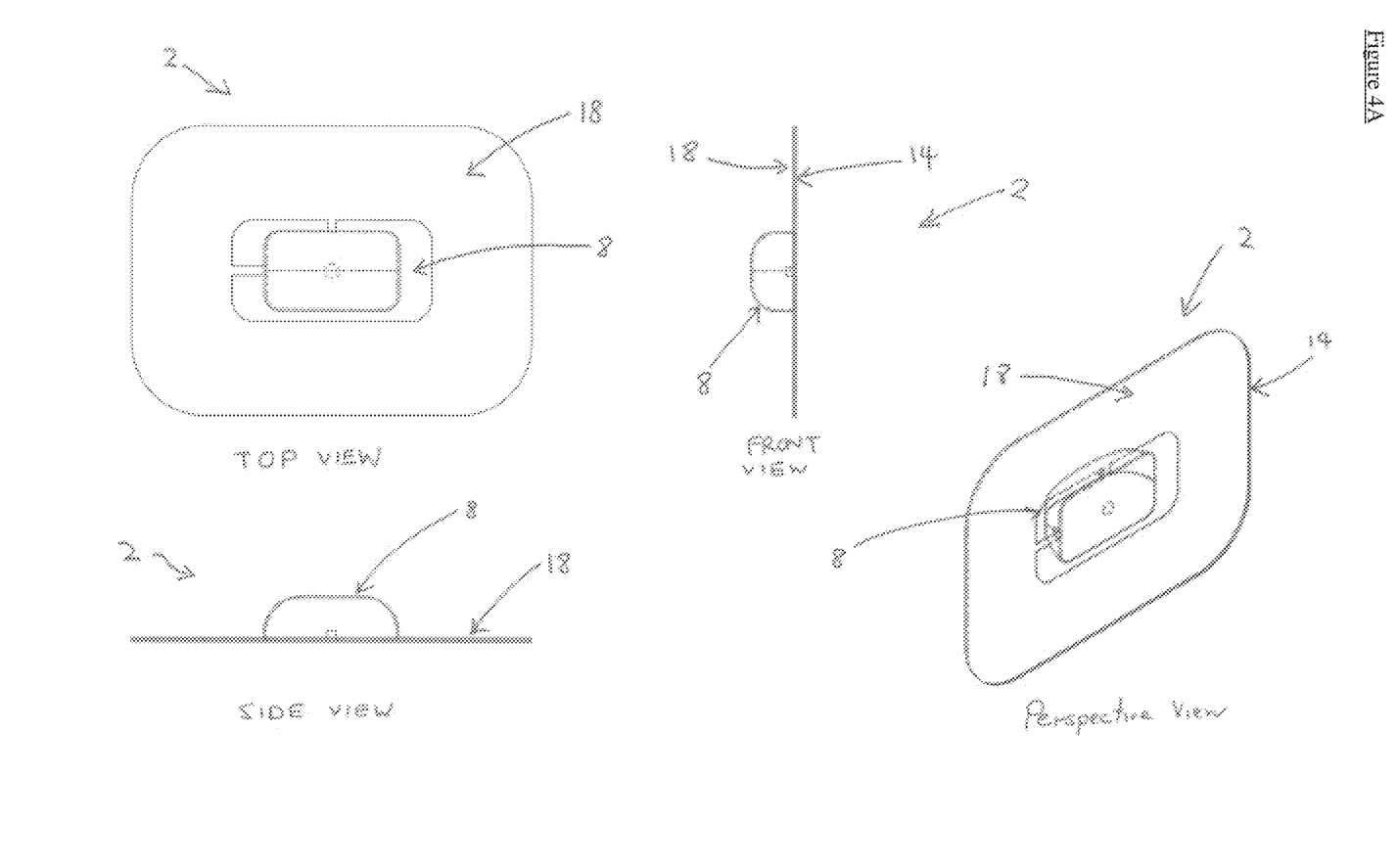
FIG. 4A is a top, front, side and perspective view of a temperature monitoring device.
Figure 4B:
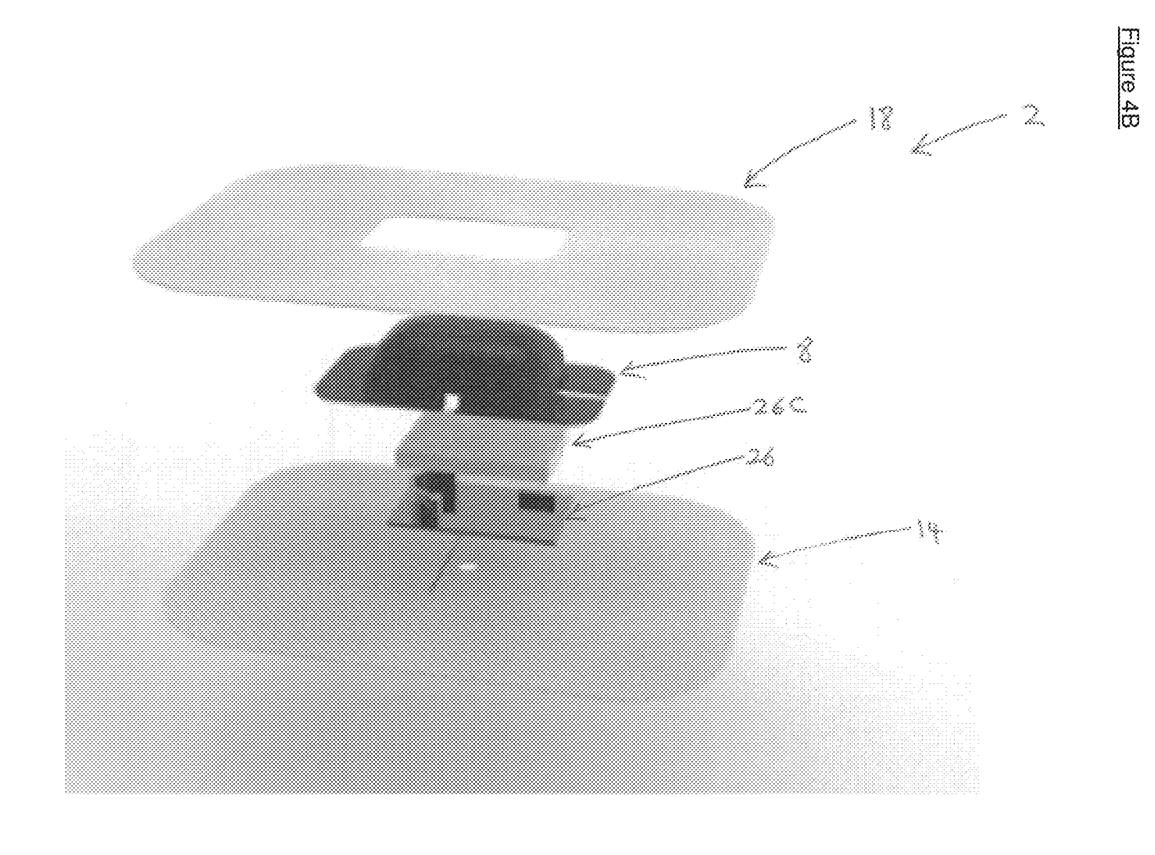
FIG. 4B is an exploded view of a temperature monitoring device of FIG. 4A.

With reference to FIGS. 4A and 4B, there is illustrated another embodiment of the temperature monitoring device 2. Similar to the embodiment as shown in FIGS. 1, 2 and 3, in this embodiment, the device 2 also includes a base which is arranged to have an attachment means in the form of a layer of dry surgical tape 14 extending away from the body 8 so as to form an annular flange around the body 8, as is similar to the embodiments of the device shown in FIGS. 1, 2 and 3. As shown in this example embodiment, the base is integrated with the annular flange and thus both the annular flange and the base are made from a single layer of dry surgical tape 14, although the base portion may also be separated from the annular flange if this is necessary by design to support the weight of the components within the housing. This surgical tape may also be manipulated by a user to bond with an animal by peeling away a liner paper which would be bonded to the adhesive side of the surgical tape when the user desires to use the device 2.

As shown in this example, the body 8, includes a printed circuit board (PCB) 26 which is implemented to include a plurality of sensors, including the temperature sensor 20 as well as processing electronics and communication gateways. This PCB 26 may also be protected by a resilient member, such as a foam cushion 26C which is disposed adjacent to the PCB 26 within the housing 8 so as to protect the PCB 26 from physical force, temperature variations and moisture. Preferably, in this example embodiment, the base portion and the annular flange of surgical tape extends a larger surface area than the embodiment as shown in FIGS. 1 to 3, with a body 8 being relatively smaller when compared with the overall size of the device. One advantage of this example embodiment is that the larger surface area of the annular flange of surgical tape allows for a greater bonding area to be provided by the device 2, and thus reducing the risk that the device 2 will detach from the animal when in use.

Figure 5:
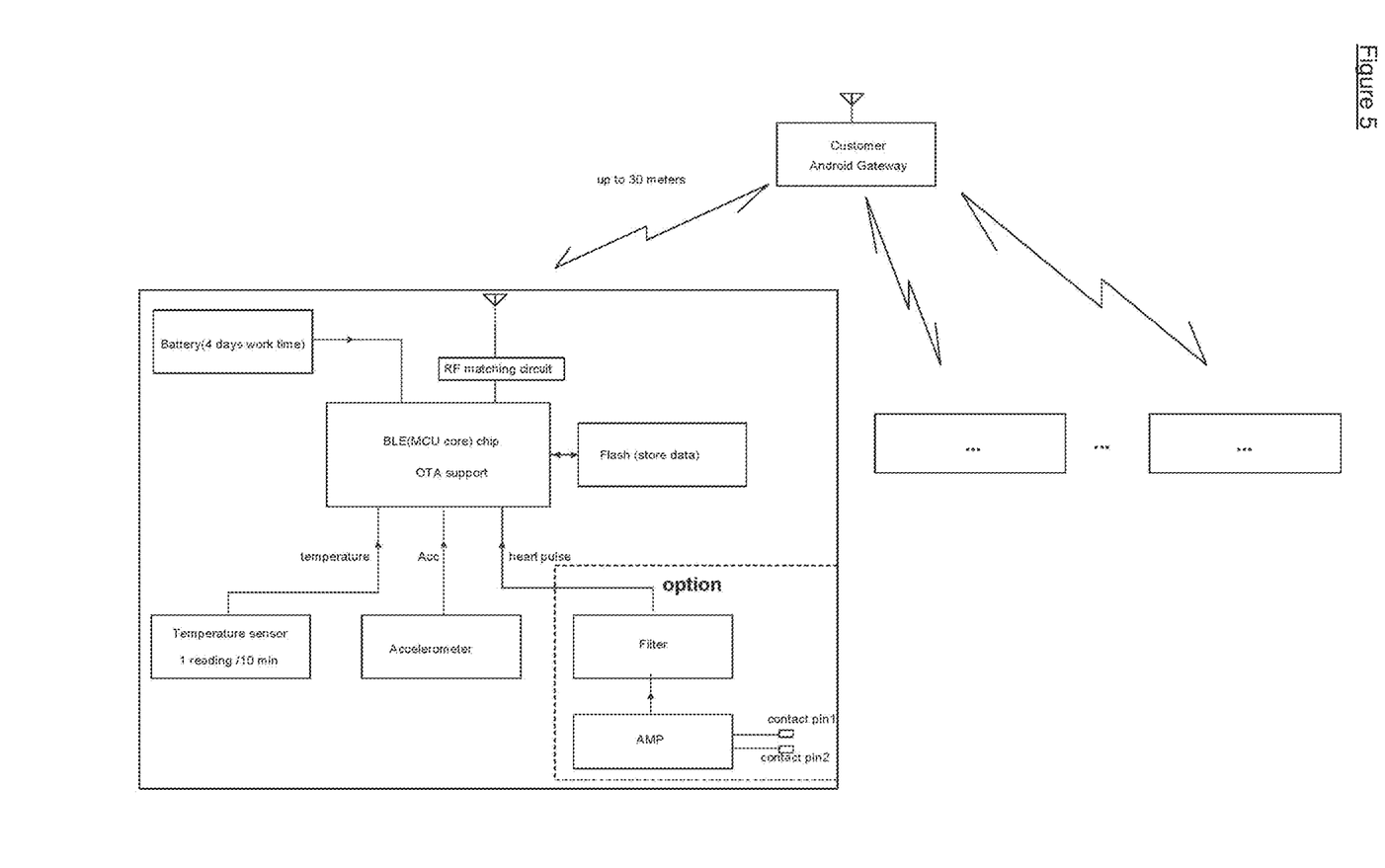
FIG. 5 is a schematic view of the circuitry of a temperature monitoring device.

With reference to FIG. 5, there is illustrated a schematic view of a system for monitoring animal temperature comprising: one or more temperature monitoring devices arranged to record the animal temperatures over a predefined time period; a communication gateway arranged to communicate with the one or more temperature monitoring devices to receive the animal temperatures over the predefined time period; and a reporting engine (not shown) arranged to process the animal temperatures for reporting a condition of the animal.

In this example embodiment, the system includes one or more temperature monitoring devices, 2, 2', 2" are arranged to be in communication 52 with a computer server or any other computing device that includes a reporting engine arranged to process the animal temperatures or other sensor data to report and or determine the condition of the animal. The communication 52 may be performed via a communication gateway, which is, in one example, an Android® gateway 32 suitable for communications with Android operating system devices. This is particularly advantageous in that the computing device that includes the reporting engine may be an Android operating system device, such as a smart phone or tablet computer, although as a person skilled in the art would appreciate, any computing system with any operating system may also be implemented with a reporting engine either by software, hardware or a combination of both.

Preferably, the communication 52 between each temperature monitoring devices, 2, 2', 2", and a computer system arranged to process and store the recorded temperatures for reporting or diagnoses, may take place via a horse groomer's smart phone, tablet computer or portable computer. In these examples, each temperature monitoring device 2, 2', 2" is arranged to communicate with a horse groomer's smart phone, via a telecommunication protocol, such as Bluetooth, Bluetooth LTE, Wi-Fi, Infrared, Near field communication (NFC), etc. Thus reducing the energy used to communicate with an external device. The data that is communicated to the groom's smart phone or portable computing device can then be processed and further uploaded to a cloud based server situation elsewhere for further processing, reporting or storage.

In situations where a travelling groom's smart phone or portable computing device is unavailable, such as when the animal is in transit, the device 2, 2', 2", may store all recorded information into memory and proceed to synchronize this information when it next connects with a travelling groom's smart phone or portable computing device. Alternatively, the device 2, 2', 2" may communicate with a portable network router or communication interface (dongle) that may be placed proximate to each animal, in turn allowing this information to be communicated to a server for distribution.

In yet another embodiment, the device 2, 2' 2" may also be implemented with telephony functionality arranged to allow the device 2, 2' 2" to communicate with a cloud or network server via a telephone network. In examples where the travelling groom's smart phone is unavailable, the device 2, 2' 2" may then proceed to upload any temperature data stored within to a cloud or network server. This information can in turn be downloaded onto the travelling groom's smart phone or portable computer.

As shown in this diagram, the printed circuit board (PCB) of each device 2, 2' 2" comprises a central processing unit 34 such as a BLE (Bluetooth Low Energy) microprocessor (MCU) with over-the-air (OTA) support arranged to execute operating instructions so as to monitor the temperature of the animal, a battery 36 for powering the device for a period of time (e.g. 4 days or more) once activated, flash memory 38 for data storage and an RF matching circuit 40 connected to an antenna 22 so as to communicate with the communication gateway.

In this example, each of the devices 2, 2' and 2" are applied onto one or more animals, such as one or more race horses being transported. The devices are then energized by the user who may remove the tag 24 to form the electrical connection between the battery and the PCB. Once energized, the microprocessor receives data from sensors such as a temperature sensor 42 which provides a temperature reading either continuously or preferably, every 10 minutes when used with race horses, although other predetermined intervals or measurement frequency may also be predefined by the user.

In a preferred embodiment as shown in FIG. 5, the device 2, 2', 2" may also have an accelerometer 44 which is arranged to detect or sense movement data that relates to the movement of the animal, and optionally a heart pulse monitor 46 comprising a filter 48, amplifier 50. The heart pulse monitor is arranged to detect and measure the heart rate of the horse whilst the filter 48 and amplifier 50 assists with improving the quality of the heart rate measurements, which may be difficult to detect or may include a lot of noise within its detected signals.

In use, once the monitoring device has been placed under the tail, a calibration factor can be calculated by measuring the actual rectal temperature with a digital thermometer and then inputting this reading into the application. Alternatively no rectal temperature reading is taken, the application can be configure to use a pre-set calibration factor such as 1.5° F. or any other suitable calibration factor.

Preferably as shown in FIG. 5, a computer server, computing device or a smartphone or tablet computer can be connected to the gateway 32 so as to receive data from multiple horses simultaneously. The data can then in turn be processed or visually presented by the reporting engine to a user such that a signal or alert to the user can be generated if there is any indication of a fever or any other flagged condition. As an example, the processing of the data may include the following indicators so as to establish the condition of the horse.

1. Indicator for: 95-101° F. [To identify horses in a normal range]
2. Indicator for: between 101-101.5° F. [To identify horses at the top end of the normal range]
3. Indicator for: to indicate a fever when the temperature is between 101.5-103.0° F.
4. Indicator for: when the temperature is greater than 103.0° F. [To indicate a critically high fever]
5. Indicator for: when the temperature is less than 95° F. [Indicating a loose device that needs inspecting/replacing, or a device that has fallen off]
6. Indicator for: when a signal is no longer being transmitted from the device because of a flat battery The application can be configured to send a text alert to the person monitoring the horses to indicate a temperature has developed, or ping/vibrate the mobile device regularly until acknowledged. As it would be appreciated, if the animals have different characteristics or a pre-existing condition, these indicators may be adjusted accordingly.

In an example where the system is used for the monitoring of race horses, if the horse develops a very transient 'fever' of 101.5 F it is probably significant even if the temperature reading is only present for 10 minutes and then returns to normal. At the end of the journey a graph can be created to view all temperature readings from the entire trip. This can be exported as a report together with any other treatment provided during the trip thus allowing a health care professional or caretaker to recommend further treatment of the horse or the possible postponement of any racing or equestrian activity.

Embodiments of the present invention may be advantageous in many industries, including agricultural and racing/entertainment. In the racing industry, the early detection of a horse's condition, such as pyrexia in a horse can lead to significant advancements in the well-being of race horses. In turn, this can improve the animal welfare, efficiencies and operational costs in the racing industry.

In one embodiment, the one or more temperature monitoring devices includes a biosensor which is arranged to detect and quantify levels of specific biomarkers in the blood or interstitial fluid, preferably in real-time. These specific biomarkers may be relevant to identifying illness, and monitoring the response of the animal to treatment. In the horse the most important biomarkers of inflammation are the Acute Phase Proteins (Such as Serum Amyloid A [SAA] and Fibrinogen).

In one example embodiment, the biosensor is arranged to detect viruses, bacteria, antibodies, cancerous cells, and other biochemical markers in the blood or interstitial fluid, that may be indicative of an infection, response to infection, or disease or damage to organ systems. This point-of-care, real-time, health monitoring system will revolutionise the way that disease in horses and other species are identified, treated and monitored.

Preferably, this biosensor may be implemented with a microchip sensor which has a plurality of micro-needles, arranged to be inserted or otherwise in contact with the animal, such as a horse, to measure the level of biomarker in the blood or interstitial fluid of the animal. Once these micro-needles are able to be contacted with the blood or interstitial fluid of the animal, the biomarkers can be detected by the microchip sensor. Although not required, the embodiments described with reference to the Figures can be implemented to file an application programming interface (API) or as a series of libraries for use by a developer or can be included within another software application, such as a terminal or personal computer operating system or a portable computing device operating system. Generally, as program modules include routines, programs, objects, components and data files the skilled person assisting in the performance of particular functions, will understand that the functionality of the software application may be distributed across a number of routines, objects or components to achieve the same functionality.

It will be appreciated by persons skilled in the art that numerous variations and/or modifications may be made to the present invention as shown in the specific embodiments without departing from the spirit or scope of the invention as broadly described. The present embodiments are, therefore, to be considered in all respects as illustrative and not restrictive. It will also be appreciated by persons skilled in the art that the present invention may also include further additional modifications made to the device which does not affect the overall functioning of the device.

It will also be appreciated that where the methods and systems of the present invention are either wholly implemented by computing system or partly implemented by computing systems then any appropriate computing system architecture may be utilized. This will include stand-alone computers, network computers and dedicated hardware devices. Where the terms "computing system" and "computing device" are used, these terms are intended to cover any appropriate arrangement of computer hardware capable of implementing the function described.

Any reference to prior art contained herein is not to be taken as an admission that the information is common general knowledge, unless otherwise indicated. It is to be understood that, if any prior art information is referred to herein, such reference does not constitute an admission that the information forms a part of the common general knowledge in the art, any other country.

The invention claimed is:

1. A health monitoring device comprising:
   a housing including a body, and a base with a first aperture;
   a temperature sensor mounted on a printed circuit board housed within the body and arranged to measure temperature of an animal in direct contact with the temperature sensor;
   a wireless transmitter for transmitting the measured temperature;
   wherein the base is provided with a first layer of adhesive tape for attaching the base to the animal, wherein the first layer of adhesive tape is defined with a second aperture aligned with the first aperture of the base;
   wherein the temperature sensor at least partly extends through both the first aperture of the base and the second aperture of the first layer of adhesive tape, such that the temperature sensor contacts the animal; and
   wherein the health monitoring device further comprises a second layer of adhesive tape to secure the body to the base via the first layer of adhesive tape, in which the first layer of adhesive tape is defined with an outer portion extending beyond an underside of the base, the body includes a peripheral margin, and the second layer of adhesive tape is provided in a form of a ring which fits over the body of the housing and includes an outer portion which extends beyond the peripheral margin of the body, the outer portion of the second layer of adhesive tape being securable to the outer portion of the first layer of adhesive tape.

2. The health monitoring device according to claim 1, wherein the first layer of adhesive tape and second layer of adhesive tape comprise medical tape or dry surgical tape.

3. The health monitoring device according to claim 1, wherein the wireless transmitter is capable of transmitting any or any combination of WiFi, Bluetooth, and Infra-red.

4. The health monitoring device according to claim 1, wherein the body includes a battery and a pull tab connected to a plastic spacer strip between the battery and an electrical contact, such that removing the plastic spacer strip via the pull tab activates the health monitoring device.

5. The health monitoring device according to claim 1, wherein the housing is shaped and sized to fit in a space between a tail and an anus of the animal.

6. The health monitoring device according to claim 1, wherein the animal is a horse.

7. The health monitoring device according to claim 1, further comprising a receiver including an application on a mobile device which can transmit an alert for selected indicators to a predetermined person.

8. The health monitoring device according to claim 7, further comprising an indicator including any or any combination of the following: normal temperature range, top end of normal temperature range, fever, critically high fever, low temperature, and/or no signal.

9. The health monitoring device according to claim 1, further comprising a heart rate sensor arranged to monitor a heart rate of the animal and/or a motion sensor arranged to detect a physical movement of the animal.

10. The health monitoring device according to claim 1, wherein each of the first layer of dry surgical tape and the second layer of dry surgical tape comprises adhesives on one side of each of the first and the second layer of dry surgical tapes, such that the first layer of dry surgical tape is capable of adhering to a skin surface of the animal, and the second layer of dry surgical tape is capable of adhering to the housing at the peripheral margin of the body and an opposite side of the first layer of dry surgical tape extending from the base so as to secure the body to the base.

11. The health monitoring device according to claim 1, further comprising a biosensor arranged to detect at least one of viruses, bacteria, antibodies, cancerous cells, and biomarkers in blood or interstitial fluid of the animal.

12. The health monitoring device according to claim 11, wherein the biosensor comprises a microchip sensor having a plurality of micro-needles, arranged to be inserted or in contact with the animal, so as to detect the at least one of viruses, bacteria, antibodies, cancerous cells, and biomarkers in the blood or the interstitial fluid of the animal.

13. The health monitoring device according to claim 12, wherein the biomarkers includes at least one of Acute Phase Proteins, Serum Amyloid A (SAA) and Fibrinogen.

14. The health monitoring device according to claim 11, wherein the biosensor is mounted on the printed circuit board housed within the body, and the biosensor at least partly extends through both the first aperture of the base and the second aperture of the first layer of dry surgical tape and to be in contact with the animal.

15. The health monitoring device according to claim 1, wherein the housing includes an insulating layer arranged to insulate the temperature sensor from an external environment.

16. The health monitoring device according to claim 1, wherein the housing includes a protective layer arranged to cushion a plurality of internal components from an external physical force.

17. A health monitoring device comprising:
- a housing including a body with a peripheral margin, and a base with a first aperture;
- a ring of dry surgical tape secured to the peripheral margin with an outer portion extending laterally beyond the peripheral margin;
- a first layer of dry surgical tape provided on an underside of the base with an outer portion extending laterally beyond the base;
- the first layer of dry surgical tape having a second aperture aligned with the first aperture in the base;
- a second layer of dry surgical tape to secure the body to the base via the first layer of dry surgical tape, wherein the second layer of dry surgical tape is provided in form of a ring which fits over the body of the housing and includes an outer portion which extends beyond the peripheral margin of the body;
- a temperature sensor at least partly extending from the body through the first aperture in the base and the second aperture in the first layer of dry surgical tape;
- a wireless transmitter and an antenna at least partly extending from the housing for transmitting temperature measurements from the temperature sensor to a wireless device running a monitoring application;
- wherein each of the first layer of dry surgical tape and the second layer of dry surgical tape comprises adhesives on one side of each of the first and the second dry surgical tapes, such that the first layer of dry surgical tape is capable of adhering to a skin surface of an animal, and the second layer of dry surgical tape is capable of adhering to the housing at the peripheral margin of the body and an opposite side of the first layer of dry surgical tape extending from the base so as to secure the body to the base;
- wherein the outer portion of the ring of the second layer of dry surgical tape is adhered to the outer portion of the layer of the first layer of dry surgical tape to secure the body to the base; and
- wherein the layer of dry surgical tape can adhere to a horse at a location beneath a tail of the horse such that the temperature sensor contacts skin of the horse;
- wherein the health monitoring device further comprises a motion sensor and a heart rate sensor, the heart rate sensor being connected to a data filter arranged to filter any readings from the heart rate sensor; and
- the heart rate sensor, the motion sensor, and the temperature sensor being disposed electronically on a printed circuit board having a microcontroller arranged to control each of the heart rate sensor, motion sensor and temperature sensor and record readings from each of the heart rate sensor, motion sensor and temperature sensor within a memory storage device;
- the memory storage device is arranged to communicate to a centralized telecommunication gateway for processing by a reporting processor arranged to process the readings from each of the heart rate sensor, the motion sensor, and temperature sensor to determine a health condition of the horse;
- the printed circuit board being housed within the housing and is surrounded by a layer of resilient shock absorbing foam disposed between the housing and the printed circuit board so as to protect the printed circuit board from shock pressure exerted on the housing;
- the printed circuit board being connected to a battery arranged to energize each of a plurality of components on the printed circuit board, wherein the battery is preinstalled within the housing during manufacturing the health monitoring device and is electronically separated from energizing the printed circuit board by a removable insulating tab having a ring pull end arranged to be pulled away by a user when in use such that the battery then forms an electrical connection with the printed circuit board and thus energizes the plurality of components on the printed circuit board; and
- wherein the health monitoring device further comprises a blood sensor mounted on the printed circuit board, and the blood sensor includes a plurality of micro-needles arranged to be inserted into the animal so as to gain access to blood or interstitial fluid of the animal for analysis by the blood sensor, the blood sensor being arranged to chemically detect for one or more biomarkers within the blood or interstitial fluid, wherein the one or more biomarkers include Acute Phase Proteins, Serum Amyloid A (SAA), and/or Fibrinogen.

\* \* \* \* \*